United States Patent [19]

Lambert et al.

[11] Patent Number: 5,322,997

[45] Date of Patent: Jun. 21, 1994

[54] OPTIC FIBER PAYOUT TEST APPARATUS HAVING A PROJECTILE TRACK SYSTEM WITH DUAL RAILS

[75] Inventors: Mark A. Lambert; Wayne A. Burnett, both of Ridgecrest; Robert A. Seberger, Weldon; James W. Harker, Lake Isabella, all of Calif.

[73] Assignee: The United States of America as represented by the Secretary of the Navy, Washington, D.C.

[21] Appl. No.: 85,895

[22] Filed: Jul. 6, 1993

[51] Int. Cl.⁵ .............................................. G01N 3/10
[52] U.S. Cl. ................................... 250/215; 73/865.3; 356/73.1
[58] Field of Search ................... 250/215, 216, 227.11; 356/73.1; 73/865.3, 865.6, 828

[56] References Cited

U.S. PATENT DOCUMENTS

| | | | |
|---|---|---|---|
| 4,911,027 | 3/1990 | White | 73/865.3 |
| 4,935,620 | 6/1990 | Schotter et al. | 230/227.11 |
| 5,103,678 | 4/1992 | Covino-Hrbacek et al. | 73/828 |
| 5,123,608 | 6/1992 | LeCompte | 242/128 |
| 5,207,106 | 5/1993 | Schwider et al. | 73/828 |

Primary Examiner—David C. Nelms
Assistant Examiner—John R. Lee
Attorney, Agent, or Firm—John L. Forrest, Jr.; Melvin J. Sliwka; Robert J. Hampsch

[57] ABSTRACT

An optic fiber payout test system and apparatus is disclosed which is adapted for simulating the payout of fiber at high speeds. This optic fiber payout test apparatus is comprised of a projectile, a source of fiber attached to the projectile, and a pneumatic propulsion system to propel the projectile and initiate the payout of the fiber. The fiber payout test apparatus further comprises a projectile track system as well as a braking system which allows the projectile to be used safely within a laboratory environment. The optic fiber payout test apparatus also provides a means for testing the payout of fiber optic cable in a manner that simulates the high rate of speed and high accelerations encountered during free flight. This capability is important for the development of launched fiber optic guided weapons systems and in particular, air launched optic guided weapons systems.

16 Claims, 5 Drawing Sheets

OPTIC FIBER PAYOUT TEST APPARATUS HAVING A PROJECTILE TRACK SYSTEM WITH DUAL RAILS

BACKGROUND OF THE INVENTION

The present invention relates in general to a optic fiber payout test system and pertains more particularly to an optic fiber payout system simulating the payout of fiber at high speeds during laboratory testing. The optic fiber payout system of this invention is an improvement over the conventional fiber payout test apparatus. This device provides a means for testing the payout of fiber optic cable in a manner that simulates the high rate of speed and high accelerations encountered during free flight. This capability is important for the development of launched fiber optic guided weapons systems and in particular, air launched optic guided weapons systems.

Prior to the development of the present invention, the primary means for performing this type of optic fiber payout testing was via captive flight testing or free flight testing. These methods of flight testing tend to be very expensive. As previously stated, an apparatus was needed to produce a high acceleration fiber optic cable payout initiation in a laboratory environment. This invention would simulate the accelerations seen by fiber optic data links during air launches and other launches from various platforms. This invention would also allow different fiber payout designs to be tested in an inexpensive and simple manner.

The launch period is known to be critical for fiber payout systems. A laboratory based test apparatus or system that simulates such launch periods for fiber payout is preferred over launching weapons from an aircraft. This is primarily due to the repeatability of a laboratory test, the ability to collect reliable data as well as the capability to control various parameters that affect the fiber payout. In addition, a laboratory based test apparatus or system is easier to use and costs less than flying an aircraft for each test. The present invention also provides a quick and easy set up for other fiber pulling needs such as fast camera coverage of payout and test ancillary equipment such as fiber payout counters, strain gauges, and other sensors.

In many fiber payout systems the wire or optic fiber typically unwinds from spools, spindles or bobbins on either the launcher or the projectile or both. A major concern with many fiber payout systems is the reliability of the payout device during the launch period. Another drawback with many fiber payout system results from the extreme forces acting upon the wire or fiber as a result of the launch as the projectile accelerates away from the launcher. Yet another concern is the formation of a relatively long spiral helix and other such phenomena know as the ballooning of the fiber as it pays out. This ballooning effect creates an increase in the tensile loading on the wire or fiber as it continues to unwind. The tensile loads present during launch tend to fracture or break the wire or fiber thereby rendering the projectile ineffective.

Yet another problem often encountered is various fiber payout systems is the phenomena of macrobending and microbending of the optic fiber and corresponding disruptions or interference in the transported signals. However, as the operational speeds of these platforms and projectiles increase, the drawbacks associated with the ballooning effects, microbending and macrobending of the fiber, as well as the tensile loading become an ever increasing problem. Simulating such ballooning effects and initial forces in order to further study and develop solutions to the aforementioned problems encountered during the operational use of fiber payout systems is a task not adequately resolved by many existing laboratory based fiber payout test apparatus or systems.

Conventional laboratory based fiber payout test systems have been used for a wide range of testing applications simulating various platforms. They have been used for example to simulate shoulder launched projectiles, mobile mounted projectiles, land based launches, and by weapons dispatched by various aerial platforms. The conventional test apparatus or system typically pulls the fiber or wire with some sort of spinning wheel at high rates of speed. These machines normally take several seconds to ramp up to speed and are not capable of generating the high acceleration seen during operational launches. These typical payout test apparatus and systems also have the drawback that they do not accurately simulate the loading that occurs during high speed payout as discussed above. This present invention, on the other hand, provides a test apparatus or system which is capable of generating a high acceleration mode in a very short period of time and simulating the actual loading that occurs during high speed payout.

SUMMARY OF THE INVENTION

The present invention is an optic fiber payout test apparatus. This optic fiber payout test apparatus is comprised of a projectile, a source of fiber attached to the projectile, and a propulsion system to propel the projectile and initiate the payout of the fiber. Preferably, the present invention further comprises a projectile track system as well as a braking system which allows the projectile to be used safely within the laboratory environment.

The preferred propulsion system is a pneumatic propulsion system which uses a piston and rod assembly operatively associated with a pneumatic power source. The preferred propulsion system further comprises a compressed air tank, an air valve which is opened by an electronic solenoid, an aluminum piston which guides a titanium rod which in turn propels the projectile. When the solenoid is activated, the air valve is forced open which allows a large volume of compressed air from the tank to an expansion cylinder where the pneumatic forces move the piston. The piston is connected to a titanium pusher rod which propels the projectile. The compressed air pushes against the piston or flat disc, forcing it through the expansion cylinder until it passes several radial exhaust holes. The compressed air from the tank escapes through the radial exhaust holes thereby reducing the pneumatic forces acting on the piston. The piston or flat disc travels further down the expansion chamber while the trapped air escapes through axial exhaust holes in the end of the piston which further act to dampen the recoil of the piston and rod assembly. During the initial expansion of the compressed air, the projectile is propelled down the track by the pusher rod.

Accordingly, it is the object of the present invention to provide an improved optic fiber payout test apparatus or system which allows the high speed and high acceleration payout of fiber or wire from launching platforms.

Another object of the present invention is to provide a high speed and high acceleration payout test apparatus that is constructed to facilitate the simple and inexpensive testing of fiber payout systems.

Yet another object of the present invention is to provide an optic fiber payout test apparatus which can accurately simulating the loading that occurs during high speed payout. With the optic fiber payout test apparatus disclosed herein, it is believed that the phenomena of optic fiber ballooning and the displacement of initial loads during operational use can be accurately simulated in a laboratory environment.

A further object of the present invention is to provide an improved fiber payout propulsion system which allows a high speed and high acceleration of the fiber in a laboratory environment, thereby substantially simulating the operational use of such payout systems on various platforms.

A feature of the present invention is that the improved optic fiber payout test apparatus or system can safely simulate operational use of fiber payout systems, including the projectile movement as well as providing the deceleration of the projectile when required.

Yet another feature of the present invention is the use of the pneumatic propulsion system to propel the projectile and initiate the optic fiber payout system. One advantage of the present system is that it simulates the high acceleration and high speed payout of fiber in an inexpensive and simple manner.

These and other objects, features and advantages of the invention are clearly evident from a thorough consideration of the figures and detailed description that follows.

DETAILED DESCRIPTION

Figure 1:
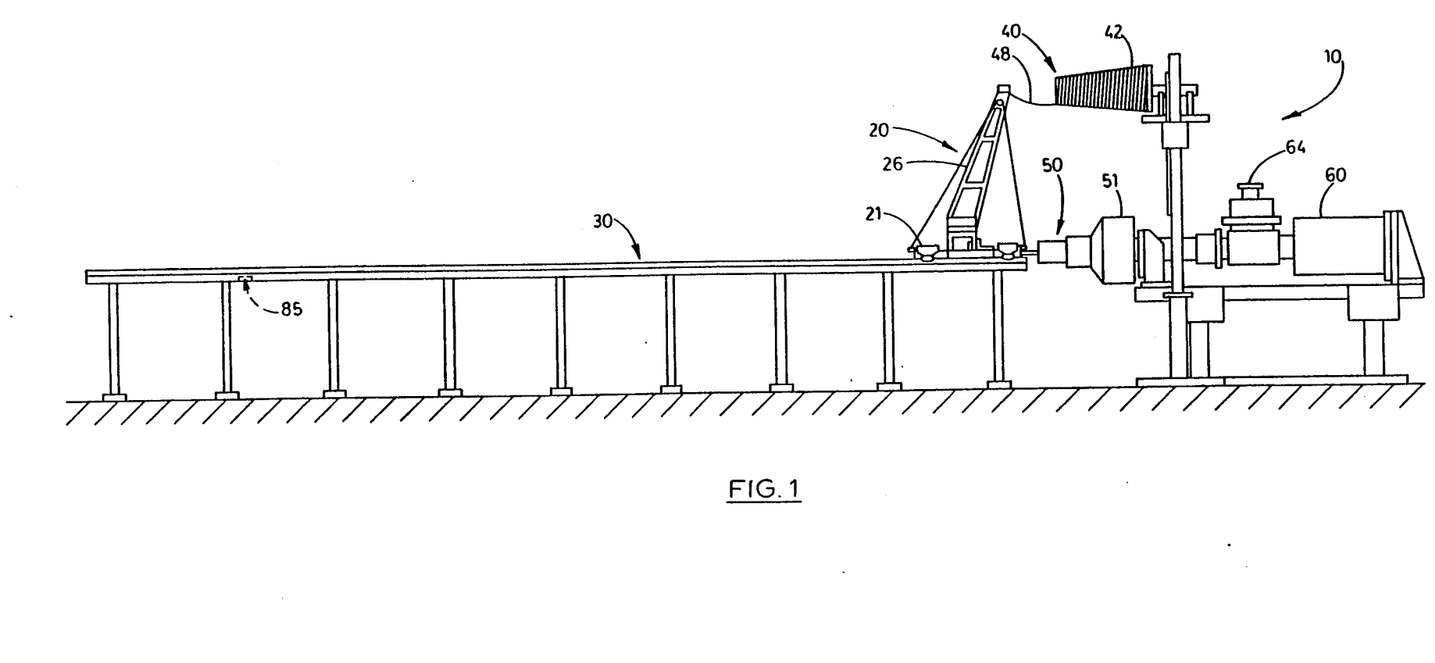
FIG. 1 is schematic view of an embodiment of the present invention.

Referring now to the drawings, there is shown in FIG. 1, a schematic of the preferred embodiment of the fiber optic payout test apparatus (10). The optic fiber payout test apparatus (10) as shown and described simulates an aircraft launch platform application which delivers a weapon system to a designated target. The optic fiber payout test apparatus (10) shown is particularly adapted for allowing greater optic fiber payout speed, greater fiber payout acceleration, and more closely simulating the actual payout forces and fiber ballooning during such high speed payout. FIG. 1 shows the optic fiber payout test apparatus (10) comprising a projectile (20), a projectile track system (30), a source of fiber (40) generally contained on a spool or a bobbin (42), and a propulsion system (50).

Figure 2:
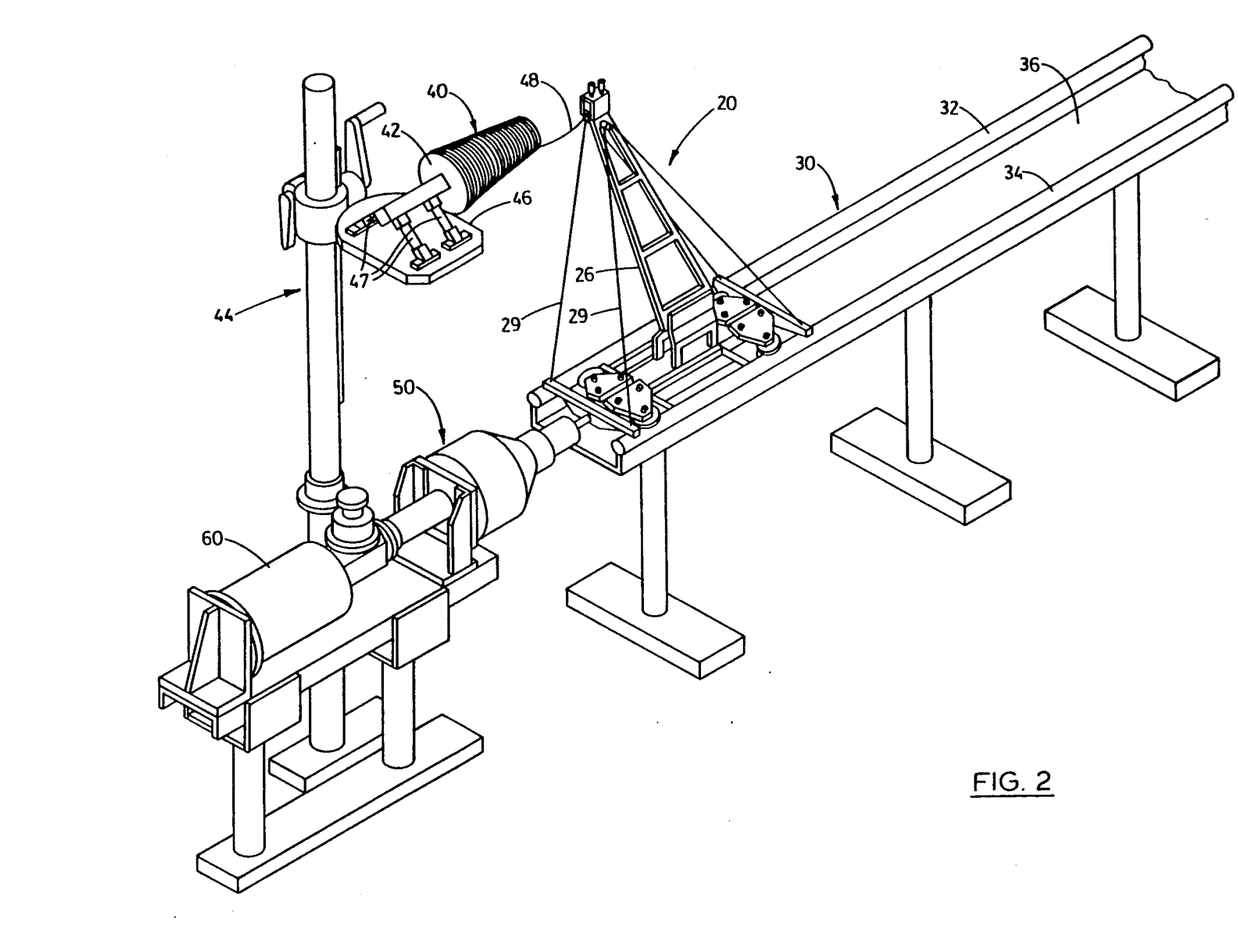
FIG. 2 is a perspective view of the source of fiber, the adjustable stand and associated equipment used in the described embodiment of the optic fiber payout test apparatus.

As pictured in FIG. 1 and FIG. 2, the source of fiber (40) is contained on a bobbin (42) which is attached to an isolated and adjustable stand (44). The bobbin (42) is cantilevered from a instrumentation mount (46) which is secured to the adjustable stand (44). The adjustable stand (44) and instrumentation mount (46) are separated from the propulsion system (50) for isolation reasons which include the need to provide adequate damping of the vibrations which affect the instruments measurements. This adjustable stand (44) may also be moved to different heights and angles relative to the projectile (20) in order to simulate various fiber payout systems. The measurement instrumentation and associated signal processing equipment used in this application are well known in the art. Specifically, the preferred embodiment of this invention utilizes a load cell (47) or load transducer which is attached to the bobbin (42) and further connected to a processing device such as an oscilloscope (not shown). The corresponding signals from the load cell (47) are then analyzed in conjunction with other measured parameters.

The bobbin (42) is suspended above the projectile (20) and projectile track system (30) to allow room for the helix of fiber to develop which typically occurs during payout of the fiber. The source of fiber (40) is preferably in the form of optic fiber (48) or cable and is wrapped or wound around the fixed bobbin (42). The following description discusses the use of an optic cable or fiber (48), however it will be understood that while the discussion is so limited, the actual scope and application of the present invention is not so limited. As mentioned above, it is also foreseeable to provide a more fully instrumented test set for measurement of various parameters such as fiber speed, bobbin rotations, fiber forces, as well as calibration of the test apparatus.

Figures 3, 4:
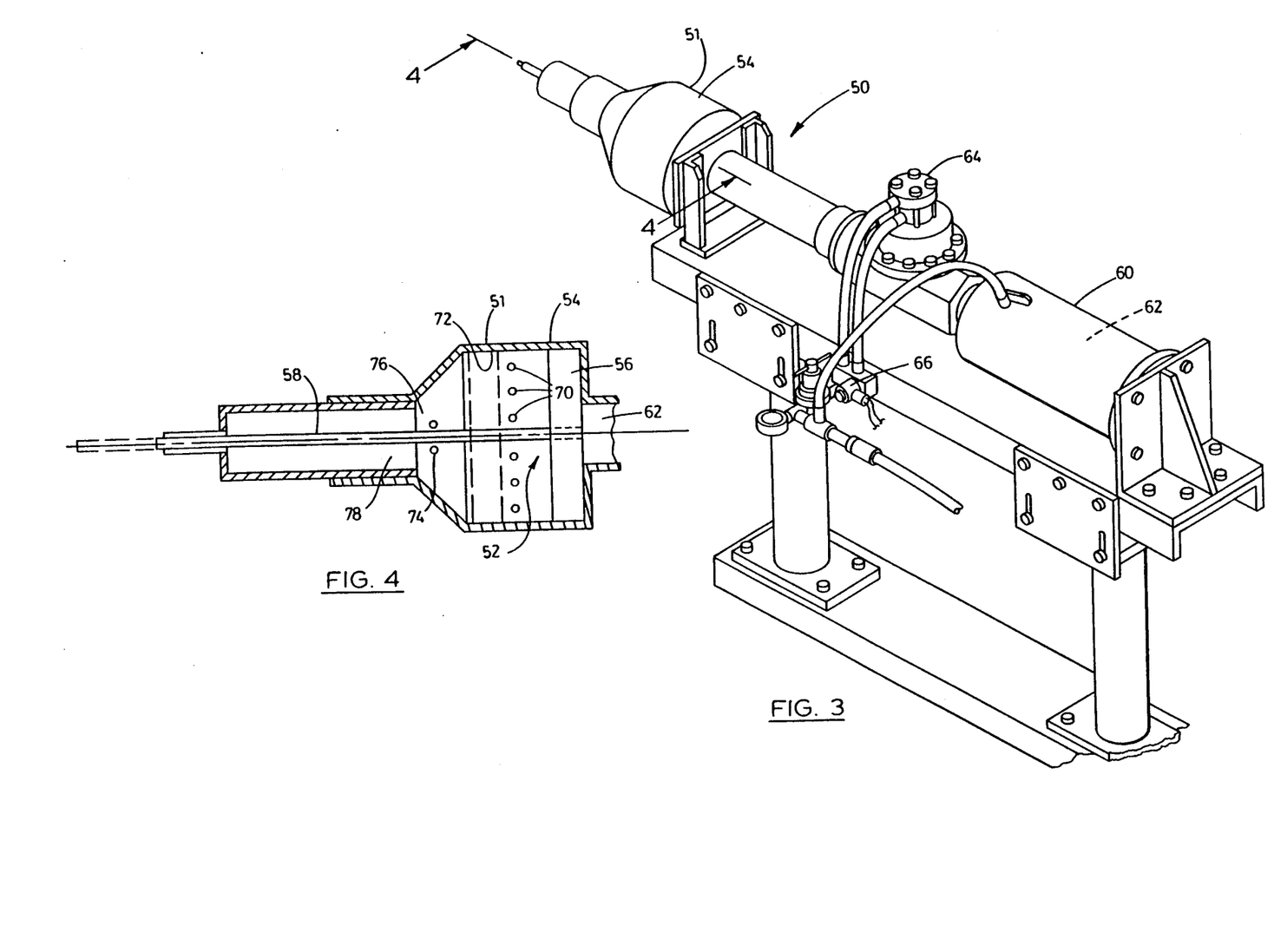
FIG. 3 is a perspective view of the propulsion system used in the described embodiment of the optic fiber payout test apparatus.
FIG. 4 is a partial cross section view of the propulsion system used in the described embodiment of the optic fiber payout test apparatus illustrating the piston and rod assembly internally disposed in the expansion chamber.

The propulsion system (50), as seen in FIGS. 1, 3, and 4 is preferably a pneumatic propulsion system (51). The disclosed pneumatic propulsion system (51) comprises a piston and rod assembly (52) which is movably disposed in an expansion cylinder (54). The expansion cylinder (54) is connected to a compressed air tank (60) filled with a compressed gas (62) to a predetermined pressure ($P_1$) by means of an air valve (64) which is opened and closed by activation of an electronic solenoid (66). The piston and rod assembly (52) preferably includes an aluminum piston (56) or flat disc, and a titanium pusher rod (58). When an electric current is passed through the electronic solenoid (66) the air valve (64) is forced open which dumps the compressed gas (62) from the compressed air tank (60) into the expansion cylinder (54). The flat disc or piston (56) inside the expansion cylinder (54) will slide within the expansion cylinder (54). This piston (56) is connected to the titanium rod (58) which in turn initiates the movement of the projectile (20) along the projectile track system (30). The electronic circuits for controlling the activation of the electronic solenoid (66) can be designed or adapted to fit the particular test set up or application in which the present fiber optic payout test apparatus (10) is used.

The compressed gas (62) expands when introduced into the expansion cylinder (54). This expansion of the compressed gas (62) pushes against the flat disc or piston (56) forcing it down the expansion cylinder (54) until it passes a series of radial exhaust holes (70) located on the radial surface (72) of the expansion cylinder (54). During the initial expansion of the compressed gas (62), the projectile (20) is propelled down the projectile track system (30) by the pusher rod (58). The compressed gas (62) from the compressed air tank (60) escapes through the radial exhaust holes (70) thereby reducing the pneumatic forces acting on the piston (56) after the initial acceleration of the projectile (20) has been attained. The piston (56) or flat disc travels further down the expansion cylinder (54) while the trapped air (78) on the opposite side of the piston (56) escapes through axial exhaust holes (74) located on the axial surface (76) at the end of the expansion cylinder (54). These axial exhaust holes (74) further act to dampen the recoil of the piston and rod assembly (52).

FIG. 1, FIG. 5, FIG. 6, and FIG. 7 further illustrate the projectile (20) used in the preferred embodiment described. The preferred projectile (20) consists of a projectile base (22), a sled (21), a plurality of grooved wheels (24), and a vertical extension (26). The preferred projectile together with the above mentioned components are constructed from light weight aluminum. The sled (21) is mounted on the projectile base (22). The grooved wheels (24) are attached to the sled (21) proximate the front and back ends of the projectile (20). The grooved wheels (24) are further oriented in a manner to allow the projectile to move freely along the projectile track system (30) without interference from the sled (21) or projectile base (22). The vertical extension (26) is centrally located on the sled (21). Within the projectile (20), or attached thereto, it is foreseeable to provide various processors and other instrumentation peculiar to the tests being conducted.

Figure 5:
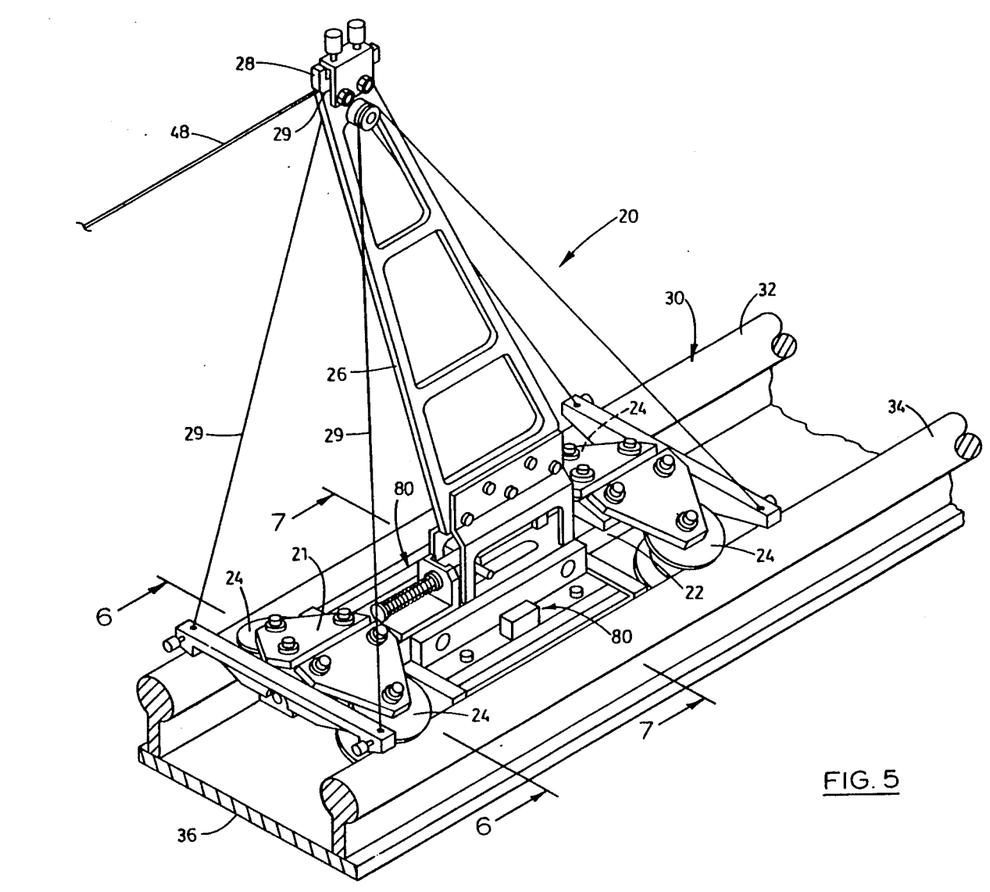
FIG. 5 is a perspective view of the projectile and the upright extension used in the described embodiment of the optic fiber payout test apparatus.

The fiber (48) or optic cable from the bobbin (42) is attached to the projectile (20) on top of the vertical extension (26) or similar fiber attachment structure. This is done to allow the fiber (48) to payout freely without interfering with the projectile track system (30). The fiber (48) is attached to the sled (21) by means of a screw friction clamp (28). In addition, a piece of hitrel, or fiber plastic coating (29), is used in the screw friction clamp (28) to protect the fiber (48). Also present in the preferred embodiment is lengths of support cable (29) which is adapted to provide stability and transfer applied forces from the vertical extension (26) to the projectile base (22).

Figure 6:
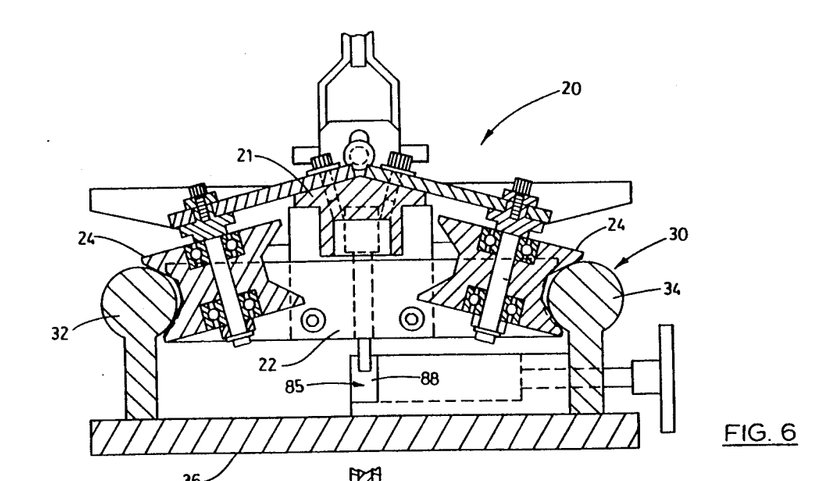
FIG. 6 is a partial cross section view of the preferred projectile in conjunction with the preferred track system illustrating the braking means in a retracted position for the described optic fiber payout test apparatus.
Figure 7:
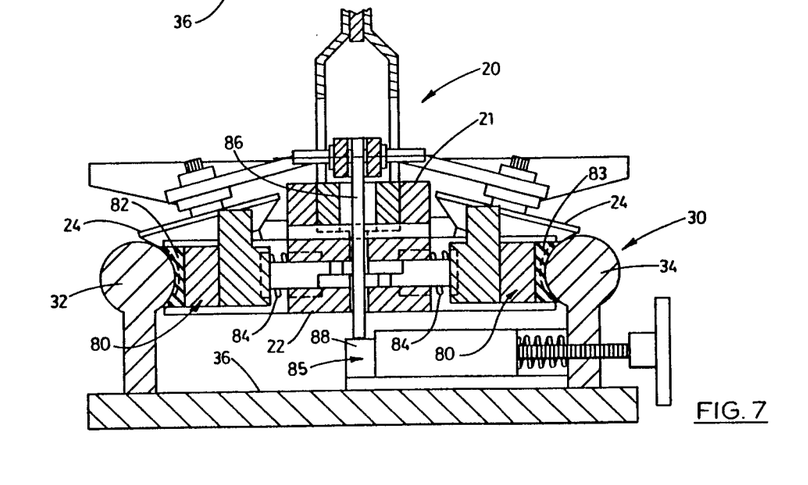
FIG. 7 is a partial cross section view of the preferred projectile in conjunction with the preferred track system illustrating the triggering mechanism wherein the braking means in an engaged position.

Also seen if FIG. 1, FIG. 6, and FIG. 7 is the preferred projectile track system (30) which is comprised of various length sections of dual rails (32,34) mounted on a common base (36) within the laboratory or test chamber. The plurality of grooved wheels (24) on the projectile are adapted to freely roll along the rails (32,34) of the projectile track system (30).

Acting in conjunction with the preferred projectile track system (30) and projectile (20) configuration is a braking system (80). Refer to FIG. 6 and FIG. 7. The braking system (80) is integral to the preferred design of the projectile (20) and operates in a safe and reliable manner. Specifically, the projectile (20) is stopped by two rubber brake pads (82,83) mounted to the projectile base (22). The brake pads (82,83) are forced against each rail (32,34) horizontally by compression springs (84) after being mechanically triggered at a specified point on the projectile track system (30). The compression springs (84) are initially biased such that the brake pads (82,83) are initially locked in a retracted position and the compression forces are orthogonally oriented with respect to the rails (32,34) of the projectile track system (30). The brake pads (82,83) are triggered with the aid of a triggering mechanism (85). Preferably the triggering mechanism consists of an arm (86), which extends below the projectile (20), which is tripped by passing a metal ramp (88) which lies between the rails (32,34) and on the common base (36) of the projectile track system (30). When this arm (86) is tripped, it allows several compression springs (84) to extend the brake pads (82,83) against the dual rails (32,34). The braking point occurs at a predetermined location on the projectile track system (30).

As discussed above, when an electric current passes through the electronic solenoid (66), the air valve (64) is opened. Removing the electric current from the electronic solenoid (66) similarly will force the air valve (64) to a closed position. When the air valve (64) is in the open position, the compressed gas (62) escapes from the compressed air tank (60) through the air valve (64) and into the expansion cylinder (54). As the compressed gas (62) expands within the expansion cylinder (54), the resulting pneumatic forces move the piston and rod assembly (52) away from the compressed air tank (60). The pusher rod (58) of the piston and rod assembly (52) is initially in contact with the projectile (20) such that movement of the piston and rod assembly (52) will result in a corresponding movement and acceleration of the projectile (20) along the projectile track system (30). The acceleration of the projectile (20) along the projectile track system (30) and away from the bobbin (42) pulls the fiber (48) off the bobbin (42) in a manner which simulates the payout of the fiber.

The projectile (20) travels down the projectile track system (30) at some predetermined acceleration and velocity which is controlled determined by the amount of pressurized gas (62) in the compressed air tank (60) which passes through the air valve (64). The projectile (20) continues moving along the projectile track system (30) until it passes the arm (86) which is part of the breaking means (80). The braking trigger mechanism (85) or device is activated which in turn forces the rubber brake pads (82,83) against the rails (32,34) to decelerate and ultimately stop the projectile (20).

Thus the optic fiber payout test system and apparatus as described simulates the forces which affect the various phenomena acting on a system for high speed optic fiber payout. This test system permits optic fiber payout to be simulated as if it were in operational use. This operation can be recorded on film for a detailed study of fiber payout dynamics. The bobbin may be connected with various instrumentation to record the longitudinal and torsional forces which are transferred to the bobbin during payout as well as measuring the payout speed or other parameters.

From the forgoing description, those skilled in the art will appreciate that all the objects and features of the present invention are realized. A high speed optic fiber payout test apparatus has been shown and described for providing the simulation of optic fiber payout from a bobbin in a laboratory environment. While a specific embodiments have been shown and described, many variations are possible. The particular shape of the bobbin, the projectile and the track system may be changed to suit the application to which it is used. The fiber material may vary, although optic fiber is preferred. The arrangement of the braking means and the propulsion system may also vary along with the introduction of particular process controllers and other equipment.

Having described the invention in detail, those skilled in the art will appreciate that modification may be made to the invention without departing from its spirit, therefor it is not intended that the scope of the invention be limited to the specific embodiment illustrated and described. Rather, it is intended that the scope of this invention be determined by the appending claims and their equivalents.

What is claimed as the invention is:

1. An optic fiber payout test apparatus comprising:
   a projectile track system having various length sections of dual rails;
   a projectile movably disposed on the projectile track system;
   a source of fiber attached to the projectile and adapted for continuous payout commensurate with the movement of the projectile;
   a propulsion system disposed in operative association with the projectile, the propulsion system further adapted to initiate the movement of the projectile along the projectile track system and initiate payout of the fiber; and
   a braking means for decelerating the projectile, the braking means disposed in conjunction with the projectile and the projectile track system.

2. The optic fiber payout test apparatus of claim 1 wherein the projectile further comprises:
   a plurality of grooved wheels which are adapted to freely roll along the rails of the projectile track system;
   a housing mounted on the plurality of grooved wheels; and
   a vertical extension adapted for securing the source of fiber to the projectile so that the payout of fiber does not interfere with the projectile track system.

3. The optic fiber payout test apparatus of claim 2 wherein the braking means further comprises:
   at least two brake pads mounted to the housing of the projectile proximate the grooved wheels;
   a plurality of compression springs connected to the brake pads and biased in a manner such that the brake pads are forced against the each of the rails in the projectile track system when the compression springs are released; and
   a mechanical trigger device disposed in operative association with the projectile track system and the projectile, the trigger means adapted to release the compression springs as the projectile passes a predetermined location on the projectile track system.

4. The optic fiber payout test apparatus of claim 3 wherein the mechanical trigger device further comprises:
   an arm attached to the housing of the projectile and extending toward the projectile track system, the arm further adapted to release the compression springs when tripped; and
   a metal ramp which is disposed between the rails of the projectile track system, the metal ramp is adapted to trip the arm so that the compression springs release which in turn force the brake pads against the rails thereby decelerating the projectile.

5. The optic fiber payout test apparatus of claim 1 wherein the source of fiber further comprises a bobbin of wound fiber suspended above the projectile and projectile track system and further cantilevered from a strain gauge mount which is further secured to an adjustable stand in a manner such that the optic fiber payout test apparatus may simulate various fiber payout systems.

6. The optic fiber payout test apparatus of claim 1 wherein the propulsion system is a pneumatic propulsion system.

7. The optic fiber payout test apparatus of claim 6 wherein the pneumatic propulsion system further comprises:
   a source of pneumatic power adapted to provide the energy required to attain a predetermined acceleration of the projectile;
   an expansion cylinder in communication with the source of pneumatic power; and
   a piston and rod assembly movably disposed in the expansion cylinder and proximate the projectile such that activation of the pneumatic source causes the movement of the piston and rod assembly which initiates movement of the projectile along the projectile track system.

8. The optic fiber payout test apparatus of claim 7 wherein the source of pneumatic power further comprises:
   a compressed air tank disposed proximate the expansion cylinder and filled to a predetermined pressure with a compressed gas;
   an air valve disposed between the compressed air tank and the expansion cylinder to regulate any flow of the compressed gas from the compressed air tank to the expansion cylinder; and
   an electronic solenoid disposed proximate expansion cylinder and in operative association with the air valve such that when an electric current is applied to the electronic solenoid the air valve opens which dumps the compressed gas from the compressed air tank into the expansion cylinder and in the absence of an electric current to the electronic solenoid the air valve closes.

9. The optic fiber payout test apparatus of claim 7 wherein the piston and rod assembly further comprises an aluminum flat disc coupled with a titanium rod movably disposed in the expansion cylinder.

10. The optic fiber payout test apparatus of claim 7 wherein the expansion cylinder further defines a plurality of radial exhaust holes on a radial surface of the expansion cylinder, the radial expansion holes act to relieve pneumatic forces acting on the piston and rod assembly after the piston and rod assembly has passed a predetermined location in the expansion cylinder.

11. The optic fiber payout test apparatus of claim 7 wherein the expansion cylinder further defines a plurality of axial exhaust holes on an axial surface of the expansion cylinder proximate the projectile, the axial exhaust holes act to dampen any recoil of the piston and rod assembly.

12. A fiber payout test apparatus comprising:
   a projectile track system having various length sections of dual rails;
   a projectile movably disposed on the projectile track system;
   a bobbin of wound fiber suspended above the projectile and projectile track system and further secured to an adjustable stand, the bobbin of wound fiber further adapted for continuous payout commensurate with the movement of the projectile;

a compressed air tank filled to a predetermined pressure with a compressed gas and located proximate the projectile and projectile track system;

an expansion cylinder in communication with the compressed air tank;

an air valve disposed between the compressed air tank and the expansion cylinder to regulate any flow of the compressed gas from the compressed air tank to the expansion cylinder;

an electronic solenoid disposed proximate expansion cylinder and in operative association with the air valve such that when an electric current is applied to the electronic solenoid the air valve opens which dumps the compressed gas from the compressed air tank into the expansion cylinder and in the absence of an electric current to the electronic solenoid the air valve closes;

a piston and rod assembly movably disposed in the expansion cylinder and proximate the projectile such that dumping of the compressed gas into the expansion cylinder causes the movement of the piston and rod assembly which initiates movement of the projectile along the projectile track system; and a braking means for decelerating the projectile, the braking means disposed in conjunction with the projectile and the projectile track system.

13. The fiber payout test apparatus of claim 12 wherein the braking means further comprises:

at least two brake pads mounted to the projectile;

a plurality of compression springs connected to the brake pads and biased in a manner such that the brake pads are forced against the each of the rails in the projectile track system when the compression springs are released; and a mechanical trigger device disposed in operative association with the projectile track system and the projectile, the trigger means adapted to release the compression springs as the projectile passes a predetermined location on the projectile track system.

14. The fiber payout test apparatus of claim 12 wherein the piston and rod assembly further comprises an aluminum flat disc coupled with a titanium rod movably disposed in the expansion cylinder.

15. The fiber payout test apparatus of claim 12 wherein the expansion cylinder further defines a plurality of radial exhaust holes on a radial surface of the expansion cylinder, the radial expansion holes act to relieve pneumatic forces acting on the piston and rod assembly after the piston and rod assembly has passed a predetermined location in the expansion cylinder.

16. The fiber payout test apparatus of claim 12 wherein the expansion cylinder further defines a plurality of axial exhaust holes on an axial surface of the expansion cylinder proximate the projectile, the axial exhaust holes act to dampen any recoil of the piston and rod assembly.

* * * * *